United States Patent
Reddy et al.

(10) Patent No.: US 7,666,450 B2
(45) Date of Patent: Feb. 23, 2010

(54) HERBAL COMPOSITIONS FOR THE REGRESSION OF CHRONIC INFLAMMATORY SKIN DISORDERS

(75) Inventors: N. B. Baktha Reddy, Chennai (IN); Vilambi N R K Reddy, Trichy (IN); Anil Torgalkar, Cranbury, NJ (US); N. Rengasamy Murugan, Trichy (IN)

(73) Assignee: Apptec, Inc., Cranbury, NJ (US)

( * ) Notice: Subject to any disclaimer, the term of this patent is extended or adjusted under 35 U.S.C. 154(b) by 0 days.

(21) Appl. No.: 11/999,057

(22) Filed: Dec. 4, 2007

(65) Prior Publication Data

US 2009/0142422 A1    Jun. 4, 2009

(51) Int. Cl.
 *A61K 36/00* (2006.01)
(52) U.S. Cl. .................................................. 424/725
(58) Field of Classification Search ............. None
See application file for complete search history.

(56) References Cited

U.S. PATENT DOCUMENTS

| | | | | | |
|---|---|---|---|---|---|
| 4,235,889 | A | * | 11/1980 | Evers | 424/727 |
| 5,165,932 | A | * | 11/1992 | Horvath | 424/764 |
| 5,858,372 | A | * | 1/1999 | Jacob | 424/195.18 |
| 6,011,067 | A | * | 1/2000 | Hersh | 514/562 |
| 2005/0084547 | A1 | * | 4/2005 | Subbiah | 424/740 |
| 2005/0152996 | A1 | * | 7/2005 | Butler | 424/725 |
| 2007/0122498 | A1 | * | 5/2007 | Reddy et al. | 424/725 |

FOREIGN PATENT DOCUMENTS

JP        07138174    *   5/1995

* cited by examiner

*Primary Examiner*—Christopher R. Tate
(74) *Attorney, Agent, or Firm*—Bregen Technical Consultants L.L.C.; Norma K. Bregen

(57) ABSTRACT

Herbal compositions that, when used in an effective amount, are suitable for the regression of chronic inflammatory skin disorders, including eczema, psoriasis and seborrheic dermatitis. The compositions, formulated as ointments, oils and shampoos, are comprised of a non-aqueous extract of *Wrightia tinctoria*, an extract of *Tragia involucrata* L., extracts of *Salix* L., *Cocos nucifera*, and pharmaceutically or cosmetically acceptable excipients suitable for topical use on humans.

3 Claims, No Drawings

HERBAL COMPOSITIONS FOR THE REGRESSION OF CHRONIC INFLAMMATORY SKIN DISORDERS

CROSS-REFERENCE TO RELATED APPLICATIONS

Not applicable.

STATEMENT REGARDING FEDERALLY SPONSORED RESEARCH OR DEVELOPMENT

Not applicable.

REFERENCE TO SEQUENCE LISTING, A TABLE, OR A COMPUTER PROGRAM LISTING COMPACT DISK APPENDIX

Not applicable.

BACKGROUND OF THE INVENTION

1. Field of the invention

The present invention relates to compositions suitable for the regression of chronic inflammatory skin disorders. In particular, the present invention relates to compositions that have been proven to be safe and effective when used for the regression of chronic inflammatory skin disorders, such as eczema, psoriasis and seborrheic dermatitis.

2. Brief Description of the Background Art

With the changing environment, food habits and lifestyle, incidences of chronic inflammatory skin disorders like eczema, psoriasis and seborrheic dermatitis are on the rise. In tandem, the cost of managing these diseases is also increasing, presenting huge challenges and opportunities to the research and development community to find alternative treatments to manage these diseases.

Chronic inflammatory skin disorders like eczema, psoriasis and seborrheic dermatitis present one or more of the symptoms including redness, skin edema, itching and dryness, with possible crusting, flaking, blistering, cracking, oozing or bleeding on the disease site. In any skin clinic, patients with chronic inflammatory disorders presenting the symptoms of eczema, psoriasis and seborrheic dermatitis will represent about 60% to 80% of the cases. Prevalence varies from country to country ranging from 25-75 per thousand of population. In the United States alone the National Institute of Health estimates that 31.6 million people have some form of eczema [A Population-Based Survey of Eczema Prevalence in the United States, Jon M. Hanifin; Michael L. Reed; Dermatitis. 2007; 18(2):82-91], The National Psoriasis Foundation estimates that the prevalence of psoriasis in western populations is around 2-3% [Benchmark survey on psoriasis and psoriatic arthritis—summary of top-line results, National Psoriasis Foundation, www.psoriasis.org].

Histologically, dermal vessel changes are marked in all stages of the diseases: vascular dilatation, tortuosity, and lymphohistiocytic proliferation. In the acute oozing stage, spongiosis is predominant. In the sub-acute moist stage, spongiosis is less in evidence and acanthosis is more predominant. In the chronic thickened stage, dermal vessel dilatation, dermal vessel tortuosity and lymphohistiocytic proliferation are seen. Common symptoms observed with eczema, psoriasis and seborrheic dermatitis may include one or more of the following: erythema, pain, pustules, dermal vessel tortuosity, spongiform pustules, granular stratulosum, skin edema, itching and dryness, with possible crusting, flaking, blistering, cracking, oozing or bleeding on the disease site. [http://en.wikipedia.org].

There are numerous therapies in the field of allopathy medicine:

Hoare C., Li Wan Po A., Williams H. (2000) Systematic reviews of treatments for atopic eczema. Health Technology Assessment 4, 1-191.

Lee, N. P., Arriola, E. R. (1999) Topical corticosteroids: back to basics. Western Journal of Medicine, 171(5-6), 351-353.

Janniger C K, Schwartz R A. Seborrheic dermatitis. Am Fam Physician (1995) 52:149-55, 159-60 [published erratum appears in Am Fam Physician 1995; 52:782]

Schwartz R, Janusz C, Janniger C (2006). "Seborrheic dermatitis: an overview". *Am Fam Physician* 74 (1): 125-30.

Scheinfeld N. (2005) Seborrheic dermatitis. *Skinmed* 4 (1): 49-50.

Luba K M, Stulberg D L. (2006) Chronic plaque psoriasis. *American Family Physician* 73 (4): 636-44.

Lebwohl M, Ting P T, Koo J Y M. (2005) Psoriasis treatment: traditional therapy. *Ann Rheum Dis.* 64 (Suppl 2).

Griffiths C E, Voorhees J J. (1996). Psoriasis, T cells and autoimmunity. *J R Soc Med.* 89 (6): 315-9.

Hunziker T, Schmidli J. Psoriasis, an autoimmune disease? Ther Umsch. (1993 February) 50(2):110-3.

Krueger G, Ellis C. Psoriasis-recent advances in understanding its pathogenesis and treatment. J Am Acad Dermatol. (2005) 53(1 Suppl 1):S94-100.

Lebwohl, M. Innovations in the treatment of psoriasis. Journal of the American Academy of Dermatology. (2004 July) 51(1)S40-41.

National Psoriasis Foundation. Psoriasis and Psoriatic Arthritis: Treatment Guide for the Health Insurance Industry. (2004) Treatment of psoriasis—Part 1—Topical Therapy and Phototherapy.

Lebwohl, M. et al, American Academy of Dermatology (October 2001) 45 (4). Treatment of psoriasis—part 2—Systemic therapies.

Lebwohl, M. et al, American Academy of Dermatology (November 2001) 45 (5); The immunological basis for the treatment of psoriasis with new biological agents.

James. G. krueger, M.D, American Academy of Dermatology (June 2002) 46, (1), 1-26; New psoriasis treatments based upon a deeper understanding of the pathogenesis of psoriasis vulgaris and psoriatic arthritis.

Callen, J. P. et al; American Academy of Dermatology, (August 2003) 49 (5), 351-356.

The treatments have been researched and developed to regress one or more symptoms of Itching erythema, pustule, pain, dermal vessel tortuosity, spongiform pustules, granular stratulosum, scaling, oozing and other symptoms common to the chronic inflammatory disorders eczema, psoriasis and seborrheic dermatitis. However, most of these therapies provide only temporary symptomatic relief and are either unsatisfactory or very expensive [National Psoriasis Conference, Boston Plaza Hotel, Aug. 5-8, 2005, Boston, Mass., USA; Wound Care Conference, Tampa, Fla., May 2007.] The therapies are associated with either short term or long term undesired side effect profiles. Herbal formulations are well known to minimize the risk of undesired side effect profiles and hence provide a viable alternative therapy to manage these disease conditions.

Research efforts to develop herbal formulations to treat these disease conditions have been on the rise.

Chopra, R. N., Nayar, S. C., and Chopra I. C., Glossary of Indian Medicinal Plants, C.S.I.R., P. 259 (1956).

Murugesa Mudaliar, K. S., Gunapadam Material Medica: Vegetable Section, Govt. of TamilNadu, P. 527 (1969).

Venkatarajan, S., Sarabendra Vaithiya Muraigal, P. 160, 161, 167 (1965).

Wealth of India, Raw Materials, Vol. X, P. 588-590, CSIR., New Delhi (1976); Yugimuni Vaidya Chintamani (800) Stanza 494-518, B. Rathina Nayakar & Sons, Viadras, India;

Nair, C. P. R., Kurup, P. B., Pillai, K. G. B., Geetha, A Ramiah, N., Effect of Nimbidin in Psoriasis, Indian Medical Journal, October 1978.

Indian Medicinal Plants: A Compendium of 500 Species, Vol. 1-5, Edited by P K. Warrier, V P K. Nambiar & C. Raman-Kutty, Published by Orient Longman (P) Ltd., 1994.

There is a continuing need to develop herbal formulations that are safe and are effective in the regression of chronic inflammatory skin disorders such as eczema, psoriasis and seborrheic dermatitis, formulations that have minimal or no side effects when used as directed.

The invention of this patent provides herbal formulations prepared from *Wrightia tinctoria, Salix* I., *Tragia involucrata* L. and *Cocos nucifera* that were tested on humans and clinically proved to be safe when used as directed and effective in treating the regression of chronic inflammatory skin disorders such as eczema, psoriasis and seborrheic dermatitis.

BRIEF SUMMARY OF THE INVENTION

It is an object of the present invention to provide herbal compositions which when used topically as directed are safe in humans and effective in the regression of chronic inflammatory skin disorders, such as eczema, psoriasis and seborrheic dermatitis. The formulations can be prepared as ointments, as oils, and as shampoos. The formulations are prepared from an effective amount of a non-aqueous herbal extract that is combined with one or more pharmaceutically or cosmetically acceptable excipients suitable for topical use.

An object of the invention is to provide an ointment, an oil and a shampoo formulation comprising an herbal composition which, when used topically in an effective amount, regresses chronic inflammatory skin disorders such as eczema, psoriasis and seborrheic dermatitis. The herbal composition comprises an effective amount of a non-aqueous herbal extract of *Wrightia tinctoria*, an herbal extract of *Salix* L., an herbal extract of *Tragia involucrata* L., an extract of *Cocos nucifera*, and one or more pharmaceutically or cosmetically acceptable excipients suitable for topical use.

BRIEF DESCRIPTION OF THE SEVERAL VIEWS OF THE DRAWING

Not applicable.

DETAILED DESCRIPTION OF THE INVENTION

The present invention relates to formulations comprising an effective amount of an herbal composition which unexpectedly provides statistically superior efficacy when compared to the recommended formulation of an allopathy control in the regression (reversal) of chronic inflammatory skin disorders, such as eczema, psoriasis and seborrheic dermatitis. The compositions have been proven to be safe when used in humans. The herbal formulations of this invention are designed specifically for topical use. They can be prepared as ointments, shampoos and oils. These compositions comprise one or more of: a non-aqueous herbal extract of *Wrightia tinctoria*, an herbal extract of *Salix* L., an herbal extract of *Tragia involucrata* L., and an herbal extract of *Cocos nucifera* combined with pharmaceutically or cosmetically acceptable excipients safe for topical use on humans.

The non-aqueous medium of the present invention for the herbal extract is a non-volatile oil, wherein the non-volatile oil is preferably a vegetable oil such as coconut oil, gingely oil, sunflower oil, corn oil, or a refined vegetable oil. The non-volatile oil in the extract of the present invention generally comprises from about 80% to 99% weight percent of the extract.

The first herbal extract in the composition suitable, when used topically in an effective amount, for the regression of chronic inflammatory skin disorders, such as eczema, psoriasis and seborrheic dermatitis, is derived from either the leaves, leafy stems, other cut portions of the *Wrightia tinctoria* plant or combination of these parts. The *Wrightia tinctoria* plant is an apocynaceae tree growing throughout India. Its flowers are white and fragrant. The other herbal extract in the topical composition suitable for regression of chronic inflammatory skin disorders, such as eczema, psoriasis and seborrheic dermatitis, is derived generally from the bark of the *Salix L.* tree, a salicaceae tree growing in Europe, North Africa and the Himalayas. The flowers are dioecious and are pollinated by bees. The active ingredient in the extract of the bark contains salicylic acid and is documented for use in skin-care products [Encyclopedia of Herbs and their uses, Dorling Kindersley, London, 1995 ISBN 0-7513-020-31]. A third herbal extract in the topical composition for the invention is derived from *Tragia involucrata* L., specifically from the root of the *Tragia involucrata* L. plant. It is a Euphorbiaceae plant growing throughout India. It is a perennial evergreen climbing hispid herb with scattered stinging hairs. The roots are bitter and diuretic and are documented for use in pruritic skin eruptions. [Indian Medicinal plants Vol. 5, Page 304, Edited by P K Warrier, V P K, Nambiar & C. Raman Kutty, Published by Orient Longman (P) Ltd., 1994].

The non-aqueous extract of *Wrightia tinctoria*, prepared at an ambient temperature, and extracts of *Salix* L. and *Tragia involucrata* L. are compounded, optionally, with other ingredients mentioned herein to prepare topical formulations of the compositions of the invention in ointment, oil and shampoo formulations. Other herbal extracts optionally in the formulation may include Melia Azardirachta Linn oils, documented to have beneficial skin effects [Nair, C. P. R., Kurup, P. B., Pillai, K. G. B., Geetha, A., and Ramiah, N., Effect of Nimbidin in Psoriasis, Indian Medical Journal, October 1978].

The herbal composition of the present invention for topical use generally comprises a non-aqueous extract of several of the active herbal ingredients in the extraction medium in the amount from 3% to 70% weight percent. The herbal extract of *Wrightia tinctoria* may be present in an amount of from 1% to 20% by weight, the herbal extract of *Tragia involucrata* L. may be present in an amount of from 1% to 20% by weight, the herbal extract of *Salix* L may be present in an amount of from 1 to 10% by weight.

The *Cocos nucifera* in the composition for regression of chronic inflammatory skin disorder such as eczema, psoriasis and seborrheic dermatitis is derived from the copra of the coconut. The copra of the coconut is dried and processed to extract the oil, which is then purified and stabilized. The extract of *Cocos nucifera* is present in the composition of the invention in the amount of from 5 to 40 weight percent.

The formulations for topical use in humans comprising the compositions of this invention includes pharmaceutically acceptable excipients such as beeswax, paraffin (liquid, soft and hard), and other standard ointment bases or equivalents to optimize use characteristics, such as consistency, spreadability, and others, manufacturability and stability. Preferentially, the topical ointment composition of the present invention generally includes at least one of the excipients taken from the group: beeswax, present in the amount of 1 to 5 weight percent of the composition, paraffin present in the amount of 5 to 40 weight percent of the composition and standard ointment bases, present in the amount of 5 to 50 weight percent of the composition.

The oil formulation comprising a composition of this invention for topical use includes pharmaceutically acceptable excipients such as vegetable oil, animal oil, and synthetic oils, such as mineral oil and liquid paraffin or their equivalent, to optimize use characteristics, manufacturability and stability. Preferentially, the oil formulation of the compounds of the present invention is comprised of excipients such as coconut oil, present in the amount of 70 to 95 weight percent of the composition.

The shampoo formulation comprising a composition of the invention includes pharmaceutically acceptable excipients, such as water, surface active agents, thickeners or viscosity enhancers, foam boosters, and stabilizers or equivalents to optimize use characteristics (for example, consistency, cleaning, spreadability, foaming) manufacturability and stability. The shampoo formulation generally comprises excipients, such as water present in the amount of 50 to 85 weight percent of the composition, surface active agents present in the amount of 10 to 30% by weight, thickeners or viscosity enhancers present in the amount of 2 to 8% by weight, foam boosters present in the amount of 2 to 6% by weight and stabilizers present in the amount of 0.5 to 2 weight percent of the composition.

In addition, formulations comprising the herbal composition that, when an effective amount is applied topically to a human, is suitable for the regression of chronic inflammatory skin disorders, such as eczema, psoriasis and sebbhoreic dermatitis, may include preservatives, coloring agents and fragrances as needed. The preservatives, coloring agents and fragrances in the ointment, oil and shampoo formulations may be present in the amount of 0-5 total weight percent of the formulation.

The use of the herbal compositions of the present invention is illustrated by the following example:

EXAMPLE

Thirty patients were enrolled in a clinical study. They were divided into two groups of 15 patients each. Group I was treated with an herbal formulation of the invention (see Table 1 for details) twice daily and Group II was treated with an allopathy control formulation (see Table 2 for details) twice daily. All patients recruited were screened to be suffering from the chronic inflammatory skin disorder eczema without any systemic complications.

TABLE 1

Herbal Ointment Formula

| No. | Ingredient | Quantity in wt. % |
|---|---|---|
| 1 | Extract of *Wrightia tinctoria* | 25% |
| 2. | Extract of *Salix* L. | 7.5% |
| 3 | Extract of *Tragia involucrata* L., | 10% |
| 4 | Extract of *Cocos nucifera* | 27% |
| 5 | Beeswax | 6% |
| 6 | Liquid paraffin | 22% |
| 7 | Coloring agent | QS |
| 8 | Fragrance | QS |

TABLE 2

Hydrocortizone Ointment (Allopathy Control)

| No. | Ingredient | Quantity in wt. % |
|---|---|---|
| 1 | Hydrocortizone | 1% |
| 2 | Standard Ointment Base | QS |

Randomization was done as per standard statistical methods to minimize bias in the study. Patients were enrolled into the study on a first come, first served basis and assigned a subject number sequentially. The assignment of each patient to the treatment group was determined by the randomization list provided by the statistician.

Each patient enrolled in the study voluntarily and each received the treatment for 8 weeks. Blood samples were collected from all patients at the beginning (T0) and at end of treatment (T8 w) for haemogram analysis, liver function testing and renal function testing to document the safety profile of the treatments administered.

The patients visited the clinic 6 times: at time t=0 w, 1 w, 2 w, 4 w, 6 w and at 8 w. During each visit the patients received a clinical examination by an expert dermatologist. The treatment sites were scored for: pain, erythema, pustules, oozing and itching to determine the efficacy of the treatment with the herbal formula as compared to the allopathy control formula.

The results of the pain measurements were scored as follows: (1) Pain is scored by the patients. (2) The intensity of the pain and the lesion was scored on a VAS scale using the scale between 0 to 100 mm where 0 represents "no pain" and 100 mm represents intolerable pain suffered by the patient. The more pain experienced by the patient, the higher the pain score.

Results of the statistical analysis of the pain measurement data for the two different groups of treatment are presented below in Table 3. A p-value of 0.05 is considered to be significant.

TABLE 3

Statistical Analysis of Measurements for Pain

| Time points (in weeks) | Group 1 (Herbal) (n = 15) | | Group 2 (Allopathy Control) (n = 15) | | Between Treatment effects | |
|---|---|---|---|---|---|---|
| | Mean | SD | Mean | SD | t statistic | p-value |
| T0 | 22 | 16.09 | 19 | 16.62 | 0.49 | 0.687 |
| T1 | 19 | 14.77 | 14 | 13.44 | 0.38 | 0.771 |
| T2 | 7 | 10.86 | 17 | 24.08 | 0.76 | 0.525 |
| T4 | 7 | 9.29 | 4 | 12.33 | 0.25 | 0.863 |
| T6 | 5 | 9.74 | 8 | 13.38 | 0.41 | 0.747 |
| T8 | 4 | 6.41 | 8 | 13.49 | 0.61 | 0.610 |
| F statistic | 5.63 | | 1.53 | | | |
| p-value | 0.000 | | 0.193 | | | |

To examine the treatment effects, a t-test was done with data between the two groups compared at the beginning and end of treatment. No statistical significance was observed (p>0.05) for treatment effects on the pain measurements at all time points (p-values ranging from 0.525 to 0.863).

To examine the time effects within each group, ANOVA analysis was done with the data within each group at all time points and F-statistic was computed. With the herbal group, there was a statistically significant time effect (p-values equal to 0.000) on the pain measurements and it was found that the pain measurement values decreased with time, suggesting a positive response to the herbal treatment over time.

However, with the allopathy control (Group II), it was found that there was no statistically significant time effect with the allopathy control formulation (p-value equal to 0.193) for pain measurement suggesting statistically no significant response to pain with the allopathy treatment over time.

The statistical data analysis clearly indicates that the herbal treatment for the regression of pain in the treatment of eczema is very effective and is superior to that of the allopathy control formulation.

Erythema was evaluated via the Draize assay on a scale of 0 to 4. [Ref: Draize, J H, et al, *J. Pharm. Exp.* 1944., *Therap. Methods for the study of irritation and toxicity of substances applied topically to the skin and mucus membranes*, 377-390] as detailed below. Erythema was scored as follows:

No erythema—0
Very slight erythema—1
Well defined erythema—2
Moderate to severe erythema—3
Severe erythema (beet redness) to eschar formation preventing grading of erythema—4

The more erythema, the higher the erythema score.

Results of the statistical analysis of the erythema measurement data for the two different groups of treatment are presented below in Table 4. A p-value of 0.05 is considered to be significant.

TABLE 4

Statistical Analysis of Measurements for Erythema

| Time points | Group 1 (Herbal) (n = 15) | | Group 2 (Allopathy Control) (n = 15) | | Between Treatment effects | |
| --- | --- | --- | --- | --- | --- | --- |
| (in weeks) | Mean | SD | Mean | SD | t statistic | p-value |
| T0 | 0.56 | 0.63 | 0.40 | 0.51 | 1.09 | 0.360 |
| T1 | 0.64 | 0.63 | 0.42 | 0.51 | 0.59 | 0.624 |
| T2 | 0.14 | 0.36 | 0.55 | 0.52 | 1.92 | 0.140 |
| T4 | 0.00 | 0.00 | 0.00 | 0.00 | 2.44 | 0.088 |
| T6 | 0.10 | 0.32 | 0.22 | 0.44 | 0.97 | 0.416 |
| T8 | 0.22 | 0.44 | 0.10 | 0.32 | 0.77 | 0.517 |
| F statistic | 3.73 | | 2.17 | | | |
| p-value | 0.005 | | 0.070 | | | |

To examine the effects of treatment, a t-test was done with data between the two groups taken at the beginning and end of the treatment. No statistical significance was observed (p>0.05) for the effect of treatment on the erythema measurements at all time points (p-values ranging from 0.088 to 0.624).

To examine the time effects within each group, ANOVA analysis was done with the data within each group at all time points and an F-statistic was computed. With the herbal group, there was a statistically significant time effect (p-values equal to 0.005) on the erythema measurements and it was found that the erythema measurement values decreased with time, suggesting a positive response to the herbal treatment over time.

However, with the allopathy control (Group II), it was found that there was no statistically significant effect over time for the allopathy control formulation (p-value equal to 0.070) for the erythema measurement, suggesting statistically no significant response on erythema to the allopathy treatment over time.

The statistical data analysis clearly indicates that the herbal treatment for regression of erythema in the treatment of eczema is very effective and is superior to the allopathy control formulation.

The results of the pustule measurements were scored as follows:

No—no pustule in the lesion—[0]
Mild—few pustule in the lesion—[1]
Moderate—pustule covering the whole lesion—[2]
Severe—pustule covering the whole lesion—[3]

The more the pustule, the higher the pustule score.

Results of the statistical analysis of the pustule measurement data for the two different groups of treatment are presented below in Table 5. A p-value of 0.05 is considered to be significant.

TABLE 5

Statistical Analysis of Measurements for Pustule
PUSTULE

| Time points | Group 1 (Herbal) (n = 15) | | Group 2 (Allopathy Control) (n = 15) | | Between Treatment effects | |
| --- | --- | --- | --- | --- | --- | --- |
| (in weeks) | Mean | SD | Mean | SD | t statistic | p-value |
| T0 | 1.06 | 0.77 | 0.93 | 0.88 | 0.40 | 0.752 |
| T1 | 0.86 | 0.66 | 0.67 | 0.89 | 0.45 | 0.772 |
| T2 | 0.40 | 0.63 | 0.64 | 0.67 | 0.78 | 0.512 |
| T4 | 0.89 | 0.60 | 0.22 | 0.67 | 1.72 | 0.186 |
| T6 | 0.36 | 0.50 | 0.50 | 0.71 | 0.08 | 0.969 |
| T8 | 0.36 | 0.67 | 0.36 | 0.67 | 0.05 | 0.987 |
| F statistic | 3.03 | | 1.26 | | | |
| p-value | 0.016 | | 0.294 | | | |

To examine the effects of treatment, a t-test was done with data between the two groups at the beginning and end of treatment. No statistical significance was observed (p>0.05) for treatment effects on the pustule measurements at all time points (p-values ranging from 0.186 to 0.987).

To examine the time effects within each group, ANOVA analysis was done with the data within each group at all time points and F-statistic was computed. With the herbal group, there was a statistically significant time effect (p-values equal to 0.016) on the pustule measurements and it was found that the pustule measurement values decreased with time, suggesting a positive response to the herbal treatment over time.

However, with the allopathy control (Group II), it was found that there was no statistically significant time effect for the allopathy control formulation (p-value equal to 0.294) for pustule measurement suggesting statistically no significant response on pustule regression to allopathy treatment with time.

The statistical data analysis clearly indicates that the herbal formulation of the invention for the regression of pustules in the treatment of eczema is very effective and is superior to the allopathy control formulation.

The results of the oozing measurements were scored as follows:

No—no oozing from the lesion—[0]
Mild—few oozing from the lesion—[1]
Moderate—oozing from the lesion—[2]
Severe—abundant oozing—[3]

The more the oozing, the higher is the oozing score.

Results of the statistical analysis of the oozing measurement data for the two different groups of treatment are presented below in Table 6. A p-value of 0.05 is considered to be significant.

TABLE 6

Statistical Analysis of Measurements for Oozing
OOZING

| Time points | Group 1 (Herbal) (n = 15) | | Group 2 (Allopathy Control) (n = 15) | | Between Treatment effects | |
|---|---|---|---|---|---|---|
| (in weeks) | Mean | SD | Mean | SD | t statistic | p-value |
| T0 | 1.00 | 0.73 | 1.20 | 0.94 | 0.40 | 0.752 |
| T1 | 0.93 | 0.62 | 0.67 | 0.78 | 0.50 | 0.684 |
| T2 | 0.40 | 0.63 | 0.55 | 0.52 | 1.26 | 0.300 |
| T4 | 0.89 | 0.60 | 0.11 | 0.33 | 2.97 | 0.050 |
| T6 | 0.36 | 0.50 | 0.40 | 0.52 | 0.51 | 0.681 |
| T8 | 0.45 | 0.69 | 0.27 | 0.47 | 0.64 | 0.594 |
| F statistic | 2.80 | | 4.19 | | | |
| p-value | 0.023 | | 0.002 | | | |

To examine the treatment effects, a t-test was done with data between the two groups at the beginning and end of treatment. No statistical significance was observed ($p \geq 0.05$) for treatment effects on the oozing measurements at all time points (p-values ranging from 0.0.050 to 0.752).

To examine the time effects within each group, an ANOVA analysis was done with the data within each group at all time points and F-statistic was computed. The herbal group demonstrated a statistically significant time effect (p-values equal to 0.023) on the oozing measurements. The oozing measurement values decreased with time suggesting a positive response to the herbal treatment with time.

Likewise, with the allopathy control (Group II), it was also found that there was a statistically significant time effect (p-values equal to 0.002) on the oozing measurements and it was found that the oozing measurement values decreased with time suggesting also a positive response to the allopathy treatment over time.

The statistical data analysis clearly indicates that the herbal treatment for the regression of oozing in the treatment of eczema is very effective and is comparable to the allopathy control formulation.

The results of the Itching measurements were scored as follows: (1) Itching was scored by the patients. (2) The intensity of the itching at the treatment site was on a VAS scale using the scale between 0 to 100 mm where 0 represents "No Itching" and 100 mm represents intolerable itching suffered by the patient. The more the itching experienced by the patient, the higher is the itching score.

Results of the statistical analysis of the itching measurement data for the two different groups of treatment are presented below in Table 7. A p-value of <0.05 is considered to be significant.

TABLE 7

Statistical Analysis of Measurements for Itching
ITCHING

| Time points | Group 1 (Herbal) (n = 15) | | Group 2 (Allopathy Control) (n = 15) | | Between Treatment effects | |
|---|---|---|---|---|---|---|
| (in weeks) | Mean | SD | Mean | SD | t statistic | p-value |
| T0 | 51 | 11.31 | 49 | 11.29 | 2.04 | 0.118 |
| T1 | 45 | 12.87 | 45 | 10.07 | 1.15 | 0.340 |
| T2 | 32 | 14.46 | 48 | 18.14 | 3.00 | 0.040 |
| T4 | 39 | 4.92 | 23 | 13.61 | 3.48 | 0.029 |
| T6 | 20 | 17.68 | 31 | 20.60 | 0.57 | 0.640 |
| T8 | 16 | 12.39 | 19 | 18.63 | 0.07 | 0.977 |
| F statistic | 14.17 | | 8.30 | | | |
| p-value | 0.000 | | 0.000 | | | |

To examine the treatment effects, a t-test was done with data between the two groups at the beginning and end of the treatment. No statistical significance was observed ($p \geq 0.05$) for the treatment effects on the itching measurements at all time points (p-values ranging from 0.118 to 0.977), except at timepoints T2 & T4 weeks.

To examine the time effects within each group, an ANOVA analysis was done with the data within each group at all time points and an F-statistic was computed. With the herbal group, there was a statistically significant time effect (p-values equal to 0.000) on the Itching measurements and it was found that the Itching measurement values decreased with time, suggesting a positive response to the herbal treatment over time.

Likewise, with the allopathy control (Group II), it was also found that there was a statistically significant effect over time (p-values equal to 0.000) on the Itching measurements and it was found that the Itching measurement values decreased with time suggesting also a positive response to the allopathy treatment over time.

The statistical data analysis clearly indicates that the herbal treatment for the regression of Itching in the treatment of eczema is very effective and is comparable to the allopathy control formulation.

The safety of the use of the herbal formulation of the present invention for the regression of eczema over the treatment period was evaluated by measuring vital signs, haemogram measurements, liver function test (LFT) measurements, and renal function test (RFT) measurements and analyzing the data as a function of time. Vital signs were measured 6 times during treatment (T0, T1 w, T2 w, T4 w, T6 w, and T8 w); Haemogram, LFT and RFT measurements were made only at the beginning and end of the treatment (T0, T8 w).

Results of the statistical analysis of the vital sign measurements (body temperature, pulse rate and respiratory measurements) are presented in Table 8. Body temperature was measured with a digital thermometer. Pulse rate was measured (beats per minute) in the radial artery by palpating the artery with the middle, index and ring finger. Respiratory rate was measured by watching the expansion of abdomen with each respiration and counting the expansions for one minute.

Friedman's chi-square test was used to analyze the data at different

TABLE 8

Statistical Analysis of Vital Sign Measurements for Herbal Treatment.
VITAL ANALYSIS for HERBAL TREATMENT (N = 15)

| Time points (in weeks) | Body Temperature (deg C.) | | Pulse Rate (/min) | | Respiration Rate (/min) | |
|---|---|---|---|---|---|---|
| | Mean | SD | Mean | SD | Mean | SD |
| T0w | 37.0 | 0.05 | 77 | 5.80 | 19 | 1.78 |
| T1w | 37.0 | 0.03 | 77 | 3.70 | 19 | 1.32 |
| T2w | 37.0 | 0.04 | 77 | 3.53 | 19 | 1.67 |
| T4w | 37.0 | 0.05 | 77 | 2.85 | 20 | 1.86 |
| T6w | 37.0 | 0.06 | 75 | 4.82 | 19 | 1.29 |
| T8w | 36.9 | 0.10 | 76 | 5.59 | 21 | 3.11 |
| Friedman's chi-square | 7.73 | | 3.73 | | 7.48 | |
| p-value | 0.172 | | 0.588 | | 0.187 | | time points for the different vital signs measurements done. The data clearly indicates that there were no statistically significant time effects on body temperature measurements ($p=0.172$); pulse rate measurements ($p=0.588$) and respiratory rate measurements ($p=0.187$) with the herbal treatment. In summary, there is no statistically significant change in vital sign measurements with time due to treatment with the herbal formulation of the present invention for the regression of eczema suggesting no safety issues.

Results of the statistical analysis of the haemogram measurements [total count of white blood cells (TC), differential white blood cells count as polymorphonuclear neutrophil (DC-P), lymphocytes (DC-L), eosinophils (DC-E) and haemoglobin (Hb)] are presented in Table 9. TC (Total count of white blood cells in the blood) was measured using Neubauer counting chamber and the normal range for TC measurements is 4000-11,000 cells per cubic millimeter. DC-P, which stands for the percentage of P-polymorphonuclear neutrophil, was measured using Neubauer counting chamber and the normal range for DC-P measurements is 55-65% of total white cell count. DC-L, which is the percentage

TABLE 9

Statistical Analysis of Haemogram Measurements for Herbal treatment.
HAEMOGRAM MEASUREMENTS FOR HERBAL TREATMENT (N = 15)

| Time points (in weeks) | TC | | Hb | | DCP | | DCL | | DCE | |
|---|---|---|---|---|---|---|---|---|---|---|
| | Mean | SD | Mean | SD | Mean | SD | Mean | SD | Mean | SD |
| T0 | 8482 | 2650 | 11.8 | 1.46 | 62 | 5.61 | 34 | 5.78 | 4 | 2.61 |
| T8 | 7709 | 911 | 11.5 | 1.24 | 60 | 3.44 | 37 | 3.67 | 3 | 1.45 |
| Paired 't' Statistics | −0.25 | | 1.69 | | 0.54 | | −0.98 | | 0.95 | |
| Sig. (2 Tailed) | 0.806 | | 0.122 | | 0.604 | | 0.350 | | 0.365 | | of lymphocytes present, was measured using Neubauer counting chamber and the normal range for DC-L measurements is 30-40% of the total white cell count. DC-L was measured. DC-E, which is the percentage of eosinophils, was measured using the Neubauer counting chamber and the normal range for DC-E measurements is 1-7% of the total white blood cell count. DC-E was measured. HB which is haemoglobin measurements was measured using RA 50 biochemical analyzer and the normal range is 12-14 gms.

To examine the time effects paired t-test was done with data at the beginning and end of treatment for the different haemogram measurements done. The data clearly indicates that there were no statistically significant time effects on TC measurements ($p=0.806$); DC-P measurements ($p=0.604$); DC-L measurements ($p=0.350$); DC-E measurements ($p=0.365$) and HB measurements ($p=0.122$) with the Herbal treatment. In summary, there is no statistically significant change in haemogram measurements with time due to treatment with the herbal formulation of the present invention for regression of eczema suggesting no safety issues.

Results of the statistical analysis of the liver function test (LFT) measurements [serum glutamic oxalo acetic transaminase (SGOT) and serum glutamic pyruvic transaminase (SGPT) are presented in Table 10. SGOT, serum glutamic-oxalo acetic transaminase (international unit per liter), was measured at visits $T_0$ and $T_{8W}$. And the normal range is 0-46 I.U./L. SGPT, serum glutamic pyruvic transaminase (international units/liter) was measured at visits $T_0$ and $T_{8W}$. And the normal SGPT ranges from 0 to 49 IU/L.

TABLE 10

Statistical Analysis of Liver Function Test (LFT) Measurements for Herbal treatment.
LFT MEASUREMENTS FOR HERBAL TREATMENT (N = 15)

| Time points (in weeks) | SGOT | | SGPT | |
|---|---|---|---|---|
| | Mean | SD | Mean | SD |
| T0 | 22 | 5.94 | 23 | 7.01 |
| T8 | 22 | 7.13 | 27 | 6.71 |
| Paired 't' Statistics | 0.07 | | 0.62 | |
| Sig. (2 Tailed) | 0.943 | | 0.560 | |

To examine the time effects paired t-test was done with data at the beginning and end of treatment for the different LFT measurements done. The data clearly indicates that there were no statistically significant time effects on SGOT measurements ($p=0.943$) and SGPT measurements ($p=0.560$) with the herbal treatment. In summary, there is no statistically significant change in LFT measurements with time due to treatment with the herbal formulation of the present invention in the regression of eczema suggesting no safety issues.

Results of the statistical analysis of the renal function test (RFT) measurements [serum creatinine and serum urea] are presented in Table 11. serum creatinine was measured at visits $T_0$ and $T_{8W}$. And the normal serum creatinine value ranges from 0.8 to 1.4 mg/dl. Serum urea was measured at visits $T_0$ and $T_{8W}$. And the normal serum urea value ranges from 10 to 50 mg/dl.

TABLE 11

Statistical Analysis of Renal Function Test (RFT) Measurements for Herbal treatment.
RFT MEASUREMENTS FOR HERBAL TREATMENT (N = 15)

| Time points (in weeks) | Serum Urea | | Serum Creatinine | |
|---|---|---|---|---|
| | Mean | SD | Mean | SD |
| T0 | 20.8 | 4.57 | 0.98 | 0.14 |
| T8 | 19.6 | 5.93 | 0.93 | 0.17 |
| Paired 't' Statistics | −0.10 | | 0.14 | |
| Sig. (2 Tailed) | 0.924 | | 0.893 | |

To examine the time effects paired t-test was done with data at the beginning and end of treatment for the different RFT measurements done. The data clearly indicates that there were no statistically significant time effects on serum creatinine measurements (p=0.893) and serum urea measurements (p=0.924) with the herbal treatment. In summary, there is no statistically significant change in RFT measurements with time due to treatment with the herbal formulation of the present invention for the regression of eczema suggesting no safety issues.

It is clear from the clinical examination and statistical analysis of the clinical data that the novel herbal formulation described in the present invention is very effective in regression of eczema. In addition, evaluation of vital signs, haemogram, LFT and RFT test results clearly show that the herbal formula of the present invention is also very safe to use on humans.

Indications of erythema, itching, oozing, pustule, and pain observed with eczema are also observed with psoriasis and seborrheic dermatitis and the topical composition for the regression of eczema described above wherein pharmaceutically or cosmetically acceptable excipients in ointment, oil and shampoo formulations may also be considered for use in management of psoriasis and seborrheic dermatitis.

Other modifications and variations of the present invention will become apparent to those skilled in the art from an examination of the above specification and examples. Therefore, other variations of the present invention may be made which fall within the scope of the appended claims, even though such variations were not specifically discussed above.

We claim:

1. An ointment suitable, when applied topically to a human, for the regression of chronic inflammatory skin disorders such as eczema, psoriasis and seborrheic dermatitis comprising:

*Wrightia tinctoria*, which has been extracted in a non-aqueous medium,
an extract of *Tragia involucrata* L.
an extract of *Salix* L,
an extract of *Cocos nucifera* and
one or more pharmaceutically or cosmetically acceptable excipients, wherein:
the non-aqueous extract of *Wrightia tinctoria* is present in an amount of from 20% to 30% by weight
the extract of *Tragia involucrata* L. is present in an amount of from 5% to 15% by weight
the extract of *Salix* L is present in an amount of from 5 to 10% by weight and
the extract of *Cocos nucifera* is present in an amount of from 25% to 30% by weight.

2. An oil-based formulation suitable, when applied topically to a human, for the regression of chronic inflammatory skin disorders such as eczema, psoriasis and seborrheic dermatitis comprising:

*Wrightia tinctoria*, which has been extracted in a non-aqueous medium,
an extract of *Tragia involucrata* L.
an extract of *Salix* L,
an extract of *Cocos nucifera* and
one or more pharmaceutically or cosmetically acceptable excipients, wherein:
the non-aqueous herbal extract of *Wrightia tinctoria* is present in an amount of from 20 to 50% by weight
the herbal extract of *Tragia involucrata* L, is present in an amount of from 10 to 30% by weight
the herbal extract of *Salix* L. is present in an amount of from 5 to 10% by weight and
the herbal extract of *Cocos nucifera* is present in an amount of from 10 to 40% by weight.

3. A shampoo formulation suitable, when applied topically to a human, for the regression of chronic inflammatory skin disorders such as eczema, psoriasis and seborrheic dermatitis comprising:

*Wrightia tinctoria*, which has been extracted in a non-aqueous medium,
an extract of *Tragia involucrata* L.
an extract of *Salix* L,
an extract of *Cocos nucifera* and
one or more pharmaceutically or cosmetically acceptable excipients, wherein:
the non-aqueous herbal extract of *Wrightia tinctoria* is present in an amount of from 0.5 to 10% by weight
the herbal extract of *Salix* L. is present in an amount of from 1 to 5% by weight
the herbal extract of *Tragia involucrata* L., is present in an amount of from 0.5 to 5% by weight and
the herbal extract of *Cocos nucifera* is present in an amount of from 0.1 to 10% by weight.

* * * * *